US007800363B2

(12) United States Patent
Bousquet et al.

(10) Patent No.: US 7,800,363 B2
(45) Date of Patent: Sep. 21, 2010

(54) METHOD AND AN INSTALLATION FOR USING EDDY CURRENTS FOR NON-DESTRUCTIVE INSPECTION WITH AUTOMATIC CALIBRATION

(75) Inventors: Sadia Bousquet, Moissy Cramayel (FR); Patrick Cabanis, Les Etards Ozouer le Voulgis (FR); Luc Ravize, Bordes (FR); Jose Claude Jacques Robin, Voisins le Bretonneux (FR)

(73) Assignee: SNECMA, Paris (FR)

( * ) Notice: Subject to any disclaimer, the term of this patent is extended or adjusted under 35 U.S.C. 154(b) by 342 days.

(21) Appl. No.: 12/104,948

(22) Filed: Apr. 17, 2008

(65) Prior Publication Data

US 2008/0265878 A1 Oct. 30, 2008

(30) Foreign Application Priority Data

Apr. 27, 2007 (FR) .................................. 07 54761

(51) Int. Cl.
*G01N 27/82* (2006.01)

(52) U.S. Cl. ...................................... 324/238; 324/202

(58) Field of Classification Search ................. 324/202, 324/219–220, 222, 228, 238–243; 702/38, 702/105
See application file for complete search history.

(56) References Cited

U.S. PATENT DOCUMENTS 6,608,478 B1 8/2003 Dziech et al.

FOREIGN PATENT DOCUMENTS

| | | | |
|---|---|---|---|
| EP | 0 410 154 | A2 | 1/1991 |
| EP | 1 452 863 | A1 | 9/2004 |
| JP | 8-15231 | | 1/1996 |

OTHER PUBLICATIONS

U.S. Appl. No. 12/123,029, filed May 19, 2008, Cabanis, et al.
U.S. Appl. No. 12/211,357, filed Sep. 16, 2008, Briffa, et al.
U.S. Appl. No. 12/436,829, filed May 7, 2009, Briffa, et al.

*Primary Examiner*—Bot L LeDynh
(74) *Attorney, Agent, or Firm*—Oblon, Spivak, McClelland, Maier & Neustadt, L.L.P.

(57) ABSTRACT

Using eddy currents for automatic inspection of a rectilinear hole formed in a metal part. An eddy-current probe is carried by a drive system associated with a positioning baseplate that carries a calibration part including a hole similar to the hole for inspection and in alignment with an orifice thereof.

5 Claims, 3 Drawing Sheets

FIG.1
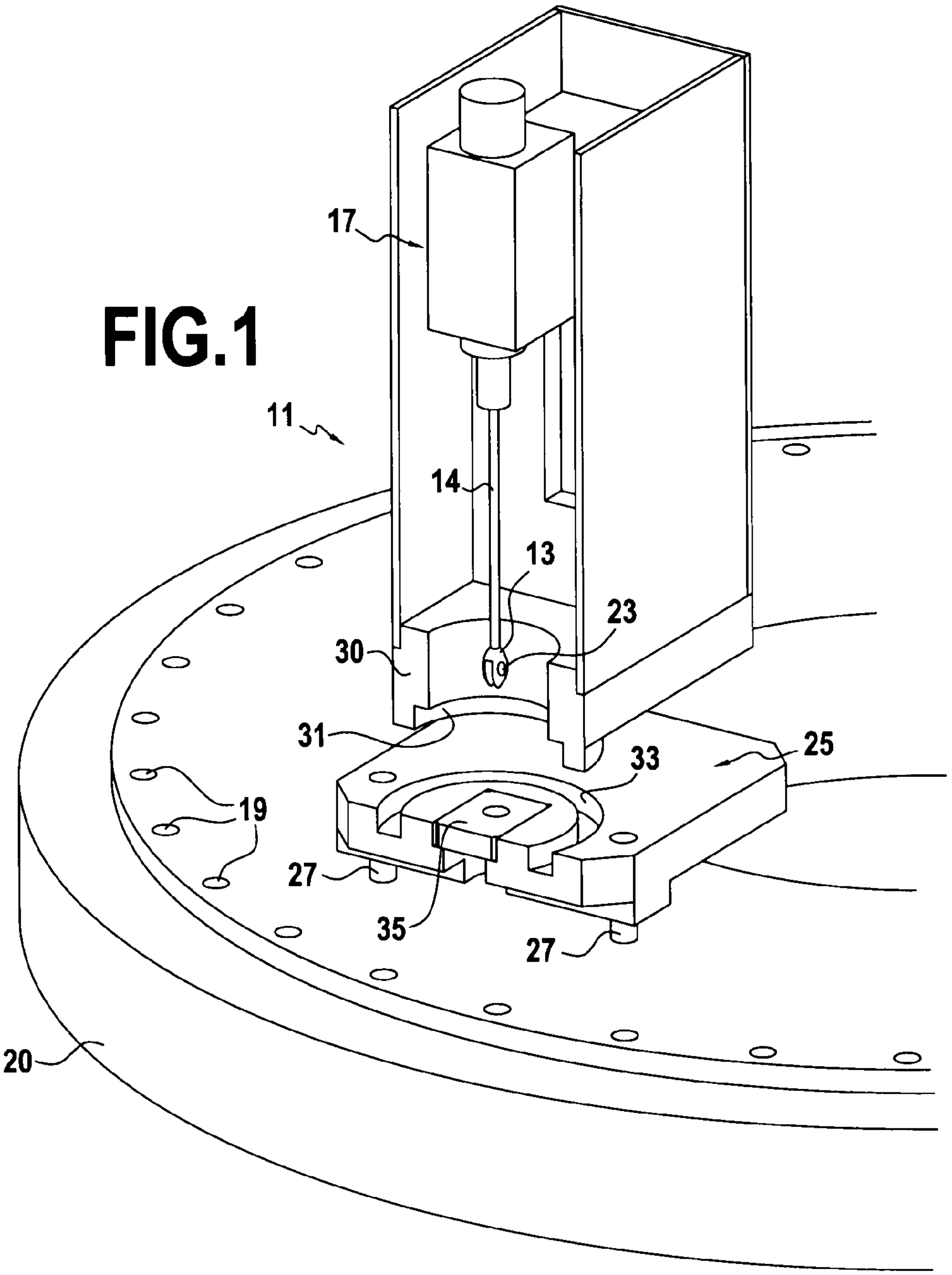
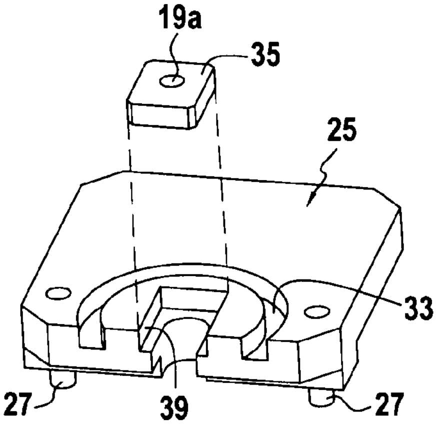
FIG.2

METHOD AND AN INSTALLATION FOR USING EDDY CURRENTS FOR NON-DESTRUCTIVE INSPECTION WITH AUTOMATIC CALIBRATION

The invention concerns the method of using eddy currents for non-destructive inspection of a hole formed in a metal part in order to detect defects that might be present at the surface of said hole or underlying said surface. This can enable fatigue cracks to be detected. The invention also provides an installation for using eddy currents for non-destructive inspection, in particular by implementing the method.

BACKGROUND OF THE INVENTION

A preferred field of application for the invention is that of inspecting fastener holes in a turbomachine disk, e.g. in an airplane engine.

Using eddy currents for non-destructive inspection consists in moving an electromagnetic sensor (a coil carrying a high frequency current) in the vicinity of a metal part for inspection, and in identifying defects (in particular non-uniformities or cavities) by detecting variations in the impedance of the sensor on passing in the vicinity of such a defect.

Such a sensor needs to be calibrated regularly with the help of a calibration part having known characteristics (e.g. including no detectable defect) that is pierced by a hole similar to the hole(s) for inspection. A hole is said to be “similar” when it comprises a borehole or a cavity having the same shape and dimensions. If it is a cavity, it need not necessarily be closed, such as the cavity of a blade root, for example.

More precisely, for the above-mentioned rotor disks, it is necessary to inspect the fastener holes in the manner mentioned above not only at the end of fabrication, but also, and mainly, during inspection for maintenance purposes. It is known to make use of an eddy-current probe carried by a drive system mounted on a support made of insulating material. The probe is installed at the end of a rod that is driven both in rotation about and in translation along its own axis. For example, the probe may have a rounded end (spherical or ellipsoidal in shape) that is split so as to present a certain amount of resilience and that includes an above-mentioned sensor. The resilience guarantees contact between the outside surface of the probe and the inside surface of the hole.

The probe is installed at the end of a rod that is driven both in rotation about and in translation along its own axis. The drive system is mounted on a support that is positioned over the orifice of a hole for inspection, and the probe is engaged in the hole in order to explore the entire surface thereof.

For calibration purposes, an operator needs to move the entire support carrying the probe and its drive means to a special stand carrying the calibration part, in order to explore completely the hole in the calibration part.

In practice, calibration is repeated once every ten holes, thereby leading to a significant loss of time, and in addition the process is not entirely satisfactory since it implies manual intervention and a change in frame of reference, thereby degrading the accuracy and the reliability of the calibration.

The invention enables those drawbacks to be overcome.

OBJECTS AND SUMMARY OF THE INVENTION

More precisely, the invention provides a method of using eddy currents for non-destructive inspection of a hole formed in a metal part, the method being of the type that consists in engaging an eddy-current probe in said hole in order to scan its inside surface, and the method consisting in associating a calibration part with said metal part, the calibration part having a hole similar to that which is to be inspected, so that said hole in the calibration part and the hole for inspection are in line with each other, then in engaging the probe successively in both of the holes in order to pick up both calibration data and data for analysis during a single stroke of the probe.

It is recalled that the above-defined method applies to using eddy currents for inspecting holes and cavities of a variety of shapes and not only for inspecting rectilinear holes with circular orifices. The two movements of the probe (in rotation and in translation) can be replaced by any other types of movement for holes of complex section. In particular, the movement imparted to the probe for inspecting a given hole may be constituted by a succession of rectilinear broaching movements, each time changing the hole generator line along which the probe is moved.

In all events, the invention is remarkable by the fact that a stage of exploring the surface or a portion of the surface of the hole is always accompanied by a calibration stage or at least by a potential calibration stage that can be performed automatically and without a change in frame of reference.

The invention also provides an installation for using eddy currents for non-destructive inspection of a hole formed in a metal part, the installation being of the type comprising an eddy-current probe carried by a probe drive system, itself associated with a positioning baseplate provided with indexing means for positioning it on said part so that the probe can be introduced into a hole for inspection, wherein said positioning baseplate carries a calibration part including a hole similar to the hole for inspection and in alignment with an orifice thereof, such that a single stroke of said probe serves to pick up both calibration data and data for analysis.

Advantageously, the positioning baseplate includes a housing shaped and dimensioned to receive an extractable and interchangeable calibration part. The metal calibration part is deemed to have no defect and can therefore be changed as a function of the kind of hole or cavity to be inspected.

BRIEF DESCRIPTION OF THE DRAWINGS

The invention can be better understood and other advantages thereof appear clearly in the light of the following description of an installation for non-destructive inspection by means of eddy currents, in accordance with the principle of the invention, given purely by way of example, and made with reference to the accompanying drawings, in which:

FIG. 1 is an exploded overall perspective view of the inspection installation in accordance with the invention;

FIG. 2 is a view of a positioning baseplate incorporating a calibration part;

MORE DETAILED DESCRIPTION

Figure 3:
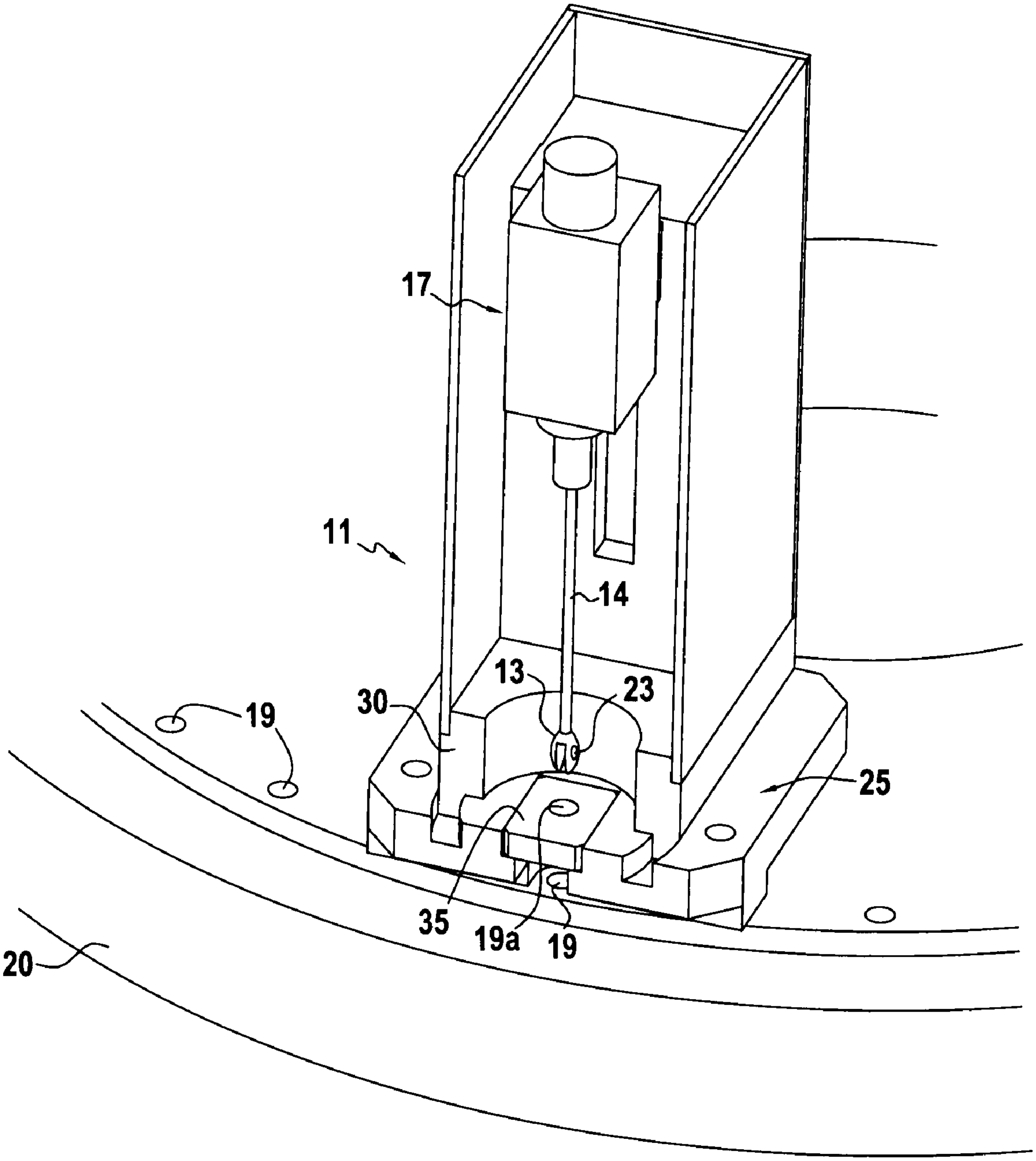
FIG. 3 shows the inspection installation in position.

The installation 11 shown comprises an eddy current probe 13 mounted at the end of the rod 14. The rod is associated with a motorized drive system 17 that, in this example, imparts two kinds of movement to the probe, movement in rotation about the axis of the rod, and movement in translation along the axis of the rod. This type of movement is well adapted to inspecting a rectilinear hole of circular section, such as for example one of the fastener holes 19 in a turbomachine disk 20. Exploration is performed at a constant speed of rotation and at a constant speed of rectilinear advance.

As mentioned above, the probe situated at the bottom end of the rod is approximately in the shape of a sphere or of an ellipsoid. It is split in a vertical plane. At rest, the diameter of the probe is slightly greater than the diameter of the hole for inspection. Consequently, as soon as the probe is introduced into the hole, the split is compressed a little and the outside surface of the probe is in contact with the inside surface of the hole. An eddy-current sensor 23 essentially constituted by a coil is integrated in the probe.

The probe drive system 17 is itself associated with a positioning baseplate 25 provided with means for fastening to the part that include the hole(s) for inspection. These fastener means include indexing means for accurately positioning them on the part so that the probe can be introduced into a hole for inspection. In this example, it can be seen that the indexing means take advantage of the fact that the holes 19 for inspection are disposed in a ring and are regularly spaced apart. Said indexing means are thus constituted by pegs 27 carried by the baseplate 25 and suitable for being engaged in the holes 19 that are adjacent to the hole that is to be inspected. Furthermore, the stand 30 of the drive system 17 includes a curved rib 31 that becomes positioned in a groove 33 of the same shape formed in the top surface of the positioning baseplate 25.

According to a remarkable characteristic of the invention, the positioning baseplate 25 carries a calibration part 35 including a hole 19*a* similar to the hole 19 for inspection. When the baseplate 25 is in position on the part 20, the hole 19*a* in the calibration part 35 is in alignment with an orifice of a hole 19 for inspection in the metal part. In this way, a single stroke of the probe 13 serves to pick up both calibration data and data for analysis. Thus, by means of the invention, calibration can be performed practically simultaneously with picking up data representative of the state of a hole for inspection (here calibration is performed shortly beforehand).

As can be seen in FIG. 2, the positioning baseplate 25 includes a housing 39 shaped and dimensioned to receive the calibration part 35, which part is extractable and interchangeable. The calibration part here is in the form of a spacer of given thickness, and made of the same metal as the part for inspection. The positioning baseplate 25 is made of an insulating synthetic material.

Figure 5:
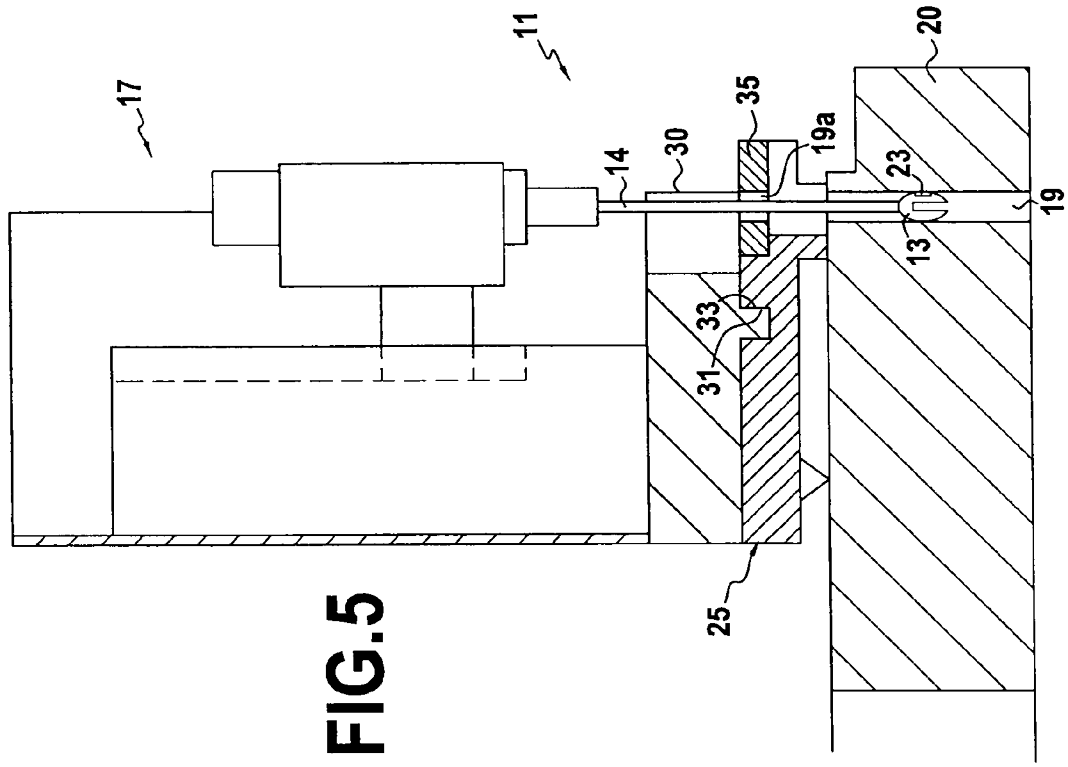
FIGS. 4 and 5 are diagrammatic views showing operation.
Figure 4:
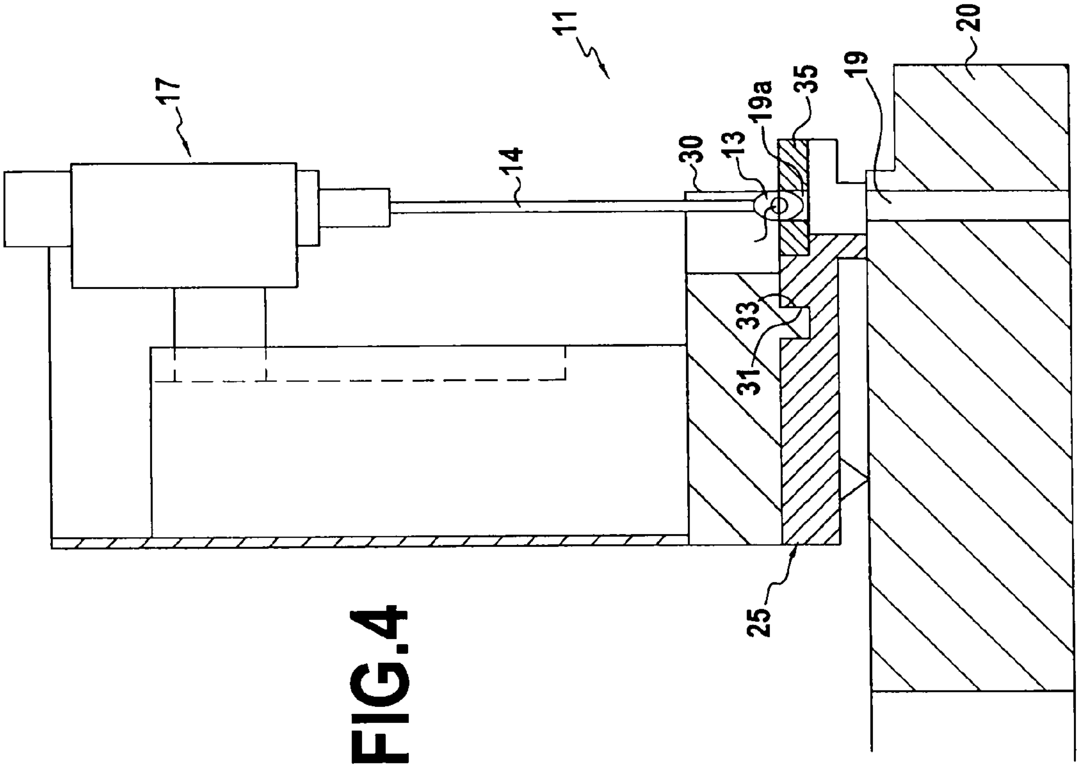

With the above-described inspection installation, the inspection process thus consists in superposing a calibration part over the metal part. The calibration part is positioned in such a manner that the hole 19*a* and one of the holes for inspection are in line with each other on the axis of the rod 14. Inspection consists in engaging the probe 13 successively in the two superposed holes (see FIGS. 4 and 5) to pick up calibration data and data for analysis during a single rectilinear and rotary stroke of the probe 13.

When inspecting a rectilinear hole of circular outline with the help of a probe in accordance with the above description, all of the data is collected during a single stroke of the probe.

In order to inspect holes or cavities of more complex shape, it is possible to proceed by means of a succession of broaching movements.

What is claimed is:

1. A method of using eddy currents for non-destructive inspection of a hole formed in a metal part, the method being of the type that consists in engaging an eddy-current probe in said hole in order to scan its inside surface, and the method consisting in associating a calibration part with said metal part, the calibration part having a hole similar to that which is to be inspected, so that said hole in the calibration part and the hole for inspection are in line with each other, then in engaging the probe successively in both of the holes in order to pick up both calibration data and data for analysis during a single stroke of the probe.

2. A method according to claim 1, wherein in order to inspect a rectilinear hole of circular section, a probe is used that is driven in rotation and that is engaged in the two superposed holes.

3. A method according to claim 2, wherein the speed of rotation and/or the speed of advance of the probe is/are constant.

4. An installation for using eddy currents for non-destructive inspection of a hole formed in a metal part, the installation being of the type comprising an eddy-current probe carried by a probe drive system itself associated with a positioning baseplate provided with indexing means for positioning it on said part so that the probe can be introduced into a hole for inspection, wherein said positioning baseplate carries a calibration part including a hole similar to the hole for inspection and in alignment with an orifice thereof, such that a single stroke of said probe serves to pick up both calibration data and data for analysis.

5. An installation according to claim 4, wherein said positioning baseplate includes a housing shaped and dimensioned to receive an extractable and interchangeable calibration part.

* * * * *